United States Patent [19]

Colegrove et al.

[11] Patent Number: 4,832,730

[45] Date of Patent: May 23, 1989

[54] SOLID, HERBICIDAL BIPYRIDINIUM QUATERNARY SALT COMPOSITIONS

[75] Inventors: George T. Colegrove, San Diego; Thomas A. Lindroth, Spring Valley, both of Calif.

[73] Assignee: Merck & Co., Inc., Rahway, N.J.

[21] Appl. No.: 685,809

[22] Filed: Dec. 24, 1984

Related U.S. Application Data

[63] Continuation-in-part of Ser. No. 639,895, Aug. 10, 1984, abandoned.

[51] Int. Cl.$^4$ ............................................. A01N 25/32
[52] U.S. Cl. .......................................... 71/92; 71/94; 71/DIG. 1; 536/3
[58] Field of Search ................. 71/DIG. 1, 92, 94, 23; 536/3

[56] References Cited

U.S. PATENT DOCUMENTS

| | | | |
|---|---|---|---|
| 2,979,499 | 4/1961 | McNeely . | |
| 3,649,239 | 3/1972 | Mitchell | 71/23 |
| 4,118,218 | 10/1978 | Drewe et al. . | |
| 4,226,855 | 10/1980 | Shigematsu | 536/3 |
| 4,401,456 | 8/1983 | Connick, Jr. | 71/88 |
| 4,764,206 | 8/1988 | Yamashiba et al. | 71/94 |

FOREIGN PATENT DOCUMENTS 46436 5/1970 Australia .
976301 11/1964 United Kingdom .

OTHER PUBLICATIONS

Tanner et al., Chem. Abst., vol. 102 (1985).
Pesticide Science, vol. 9, No. 5, Oct. 1978, pp. 425–433, P. R. F. Barrett.
93:23747x Connick, Chem. Abstract, (1980).

*Primary Examiner*—Catherine L. Mills
*Attorney, Agent, or Firm*—Gabriel Lopez; Hesna J. Pfeiffer

[57] ABSTRACT

Bipyridinium quaternary salt compositions are prepared which are dry, free-flowing, wettable powders. The solid compositions are complexes of the bipyridinium salts and algin.

10 Claims, No Drawings

SOLID, HERBICIDAL BIPYRIDINIUM QUATERNARY SALT COMPOSITIONS

CROSS REFERENCE TO RELATED APPLICATIONS

This application is a continuation in part of application Ser. No. 639,895 filed Aug. 10, 1984 now abandoned.

BACKGROUND OF THE INVENTION

Bipyridinium (also known as bipyridylium) quaternary salts such as those of U.S. Pat. No. 4,118,218 are useful herbicidal compounds. Of these, paraquat (1,1'-dimethyl-4,4'-bipyridinium dichloride) and diquat (6,7-dihydrodipyrido (1.2-a; 2'.1-c) pyrazinediium dibromide) are the most commonly used. These compounds are typically sold commercially as aqueous compositions. Attempts at preparing free flowing wettable powder formulations of these salts have not proved successful. UK No. 2,100,603 describes wettable powder compositions using powdered calcium silicate as a carrier. J5 6152-401 (Asahi Chemical) describes powdered compositions comprising inorganic sulphate salts of sodium, magnesium, etc. and anti-caking compounds such as white carbon, borax, silica gel, etc. U.S. Pat. No. 4,118,218, which is incorporated herein by reference, describes a process for preparing granular herbicidal compositions which comprises depositing an aqueous solution of the bipyridinium quaternary salts on inert carriers, preferably calcium or sodium chloride. This patent also refers to various Japanese and U.K. patent applications which teach solid herbicidal compositions. None of these compositions has been commercially successful. Generally, the prior art compounds have not been sufficiently concentrated in active ingredients, have not hydrated properly, or have not prevented crystallization of the active ingredient, thus posing a potential hazard to handlers of the dry powders. Crystallization occurs on drying of aqueous solutions of the herbical bipyridinium salts. Crystals also appear in the dry compositions of these salts.

SUMMARY OF THE INVENTION

Highly concentrated solid bipyridinium salt herbicidal compositions have now been prepared. The compositions exhibit no surface crystallization. They are prepared by mixing algin with bipyridinium salts, neutralizing the mixture to form a complex, and then drying.

DETAILED DESCRIPTION

The compositions of this invention are solid, herbicidal bipyridinium quaternary salt/algin complexes comprising 14–52% (wt.) bipyridinium salt, calculated as cation. The algin is preferably alginic acid, especially one of low viscosity (less than 20 cP, 10% solution). The bipyridinium salt is preferably one of:
1,1'-ethylene-2,2'-bipyridylium dibromide,
1,1'-dimethyl-4,4'-bipyridylium dichloride,
1,1'-di-2-hydroxyethyl-4,4'-bipyridylium dichloride,
1,1'-bis-3,5-dimethylmorpholinocarbonylmethyl-4,4'-bipyridylium dichloride
1-(2-hydroxyethyl)-1'-methyl-4,4'-bipyridylium dichloride,
1,1'-di-carbamoylmethyl-4,4'-bipyridylium dichloride,
1,1'-bis-N,N-dimethylcarbamoylmethyl-4,4'-bipyridylium dichloride,
1,1'-bis-N,N-diethylcarbamoylmethyl-4,4'-bipyridylium dichloride,
1,1'-di-(piperidinocarbonylmethyl)-4,4'-bipyridylium dichloride,
1,1'-diacetonyl-4,4'-bipyridylium dichloride,
1,1'-diethoxycarbonylmethyl-4,4'-bipyridylium dibromide, or
1,1'-diallyl-4'-bipyridylium dibromide.
Of these 1,1'-ethylene-2,2'-bipyridylium dibromide and 1,1'-4-4'-dimethyl-bipyridylium dichloride are especially preferred.

The complexes of this invention are prepared by reacting the bipyridinium salts with algin. By algin is meant alginic acid and the salts thereof. Alginic acid, derived primarily from kelp, is a commercially available product, e.g., KELACID ® (Kelco Div., Merck & Co., Inc.). The salts include appropriate metal salts e.g. alkali metal, alkaline earth metal, ammonium salts, and organic derivatives e.g. alkylene gylcol, propylene glycol and the like. The salts are preferably water soluble. The preferred salts are sodium, potassium ammonium and propylene glycol alginate. In this invention, when very rapid hydration is desired, very low viscosity alginic acid (or salt thereof) is preferred (10% solution, less than 20 cP). (All viscosities herein are as measured on a Brookfield LVT viscometer at 60 rpm, using the appropriate spindle.) When a slower hydration rate is desired, a higher viscosity alginic acid or an alginate may be used. The complexes are formed by mixing the bipyridinium salts and the algin and neutralizing the mixture. Several methods can be used; for example, pan agglomeration; drum drying, oven drying, or spray drying algin solutions; fluid bed dryer agglomeration; and precipitation by a nonsolvent of a bipyridinium/algin solution. Conveniently, neutralization is accomplished by introducing an alkali to the algin/bipyridinium salt mixture and measuring pH. Alternatively, a predetermined amount of alkali can be present in the algin or bipyridinium salt prior to mixing. Useful alkalis include ammonia, ammonium hydroxide, sodium hydroxide, and potassium hydroxide. These processes are described in greater detail below. Variations such as droplet size, drying temperature and time, concentration of ingredients, etc. are within the scope of this invention.

Pan Agglomeration

Powdered algin is placed in a pan agglomerator which produces a flowing bed of dry algin. A solution of bipyridinium salts is then sprayed onto the moving algin bed causing agglomeration of the algin powder into granules. The spray is produced through a nozzle which produces about a 500 micron droplet size. When all the algin has been agglomerated and all the bipyridinium salt solution is added, the agglomeration is then ammoniated with ammonia gas to a pH of 7.0 to 8.0, when measured on the damp granules. The complex granules are dried in a fluid bed dryer at an inlet temperature of 120° C. for 10 minutes. This produces a free flowing granular product containing a high concentration of active herbicide. A commercially available apparatus for this process is the Ferrotech Pan Agglomerator, model FC 016-02 (Ferrotech Co., Wyandotte, Mich.).

Drum Drying

The algin is mixed with the bipyridinium salt solution for ten minutes. This mixture is then ammoniated with either ammonia gas or 28% ammonium hydroxide solution. This produces a viscous, almost paste-like, liquid. After 15 minutes of additional mixing the complex is ready to be drum dried by conventional means.

Oven Drying/Spray Drying

When there is a greater amount of water in the system, instead of drum drying the complex can be dried in an oven or in conventional spray drying equipment.

Nonsolvent Precipitation

Algin is suspended in a water/non solvent mixture. The mixture should have enough water such that the algin swells but does not substantially dissolve. A 50:50 mixture of water and isopropanol is recommended. Alkali and a bipyridinium salt solution are added. This mixture is then stirred for 18 hours at ambient temperature, filtered, washed with the mixture, filtered, then dried.

Perlite

Complexes can also be obtained by blending a combination of algin and perlite with the bipyridinium salt solution. The perlite aids in absorption of the herbicide solution to improve handling properties. A 3:1 to 1:3 blend (preferably 1:1) of algin:perlite is mixed with the bipyridinium salt solution, neutralized, and dried. The product is crystal-free and easily soluble but produces a floc in aqueous solutions. Perlite is commercially available (e.g., Dicaperl HP-200, HP-210, or HP-1000; Grefco, Inc.). Because of the floc produced, perlite compositions should be limited to high solids formulations such as suspension fertilizers.

Using these processes, complexes can be prepared with high concentrations of bipyridinium salts (14–50%, calculated as cation). Advantageously, when very low viscosity alginic acid is used these complexes are easily soluble in water. Where rapid solubility is not necessary, higher viscosity alginic acid or alginate can be used. The dissolved complexes can be used with commercial spraying equipment.

The advantageous properties of the algin/bipyridinium complexes of this invention are not exhibited in other blends or complexes. Combinations with the following ingredients have been tested with paraquat.

| | Results |
|---|---|
| 1. Starch Graft Copolymers (U.S. Pat. No. 3,935,099) | Paraquat was absorbed but about 10% was permanently bound to the polymers, thus diminishing the herbicidal effect. |
| 2. Microcrystalline cellulose (Avicel 101) | Did not swell and imbibe the paraquat. |
| 3. Diatomaceous earth | Did not absorb paraquat. |
| 4. Cold water soluble tamarind gum (EP 11,951) | Paraquat was absorbed but crystallized on the particle surfaces. |
| 5. Polyacrylate solids (from Acrysol/RM-4) | Permitted crystal growth. |
| 6. Sodium lignosulfonate | Reacted with paraquat but formed insoluble precipitate. |
| 7. Carboxymethyl cellulose (Drispac Super Low) | Absorbed the paraquat but crystals formed on surface. |

The herbical use of the bipyridinium salts are well known in the art. The solid complexes of the present invention, when dissolved, are usable as herbicides in the amounts, combinations, apparatuses, methods, etc. already well known to users of bipyridinium salts.

The invention is further defined by reference to the following preparations and examples, which are intended to be illustrative and not limiting.

Preparation 1

Low Viscosity Alginic Acid

Alginic acid with a 1% viscosity of 1400 cP was treated with 1% HCl solution and heated to 90° C. for 5, 10, 15, and 20 minutes. At each time a sample was taken then and divided; one aliquot was dried at ambient, the other dried at 150° F. (65.5° C.). Algin/bipyridinium salt complexes were prepared from the samples and the solubilities measured. Table I illustrates that the solubility rate of the complex depends on the viscosity of the acid.

Increasing the drying temperatures hastens the degradation of the polymer. Thus, after 5 minutes of reaction time, the ambient temperature aliquot exhibited a viscosity of 105 cP, whereas the 65.5° C. dried aliquot exhibited 28 cP.

TABLE I

| ACID VISCOSITY VS. SOLUBILITY RATE | | |
|---|---|---|
| Reaction Time | 10% Acid Viscosity (Ambient Drying) | Solubility Time of Complex |
| 5 min. | 105 cP | 5 min. |
| 10 min. | 45 cP | 3 min. |
| 15 min. | 38 cP | 3 min. |
| 20 min. | 31 cP | 2 min. |
| 25 min. | 20 cP | 1 min. |

Using another sample of alginic acid, comparable results were obtained as shown in Table II.

TABLE II

| ACID VISCOSITY VS. SOLUBILITY RATE | |
|---|---|
| 10% Acid Viscosity (Ambient Drying) | Solubility Time of Complex |
| 1600 cP | 15 min. |
| 1000 cP | 13 min. |
| 10 cP | less than 1 min. |
| 8 cP | less than 1 min. |

Preparation 2

Low Viscosity Alginates

When it is desired to use low viscosity alginates instead of alginic acid, these salts can be prepared by standard processes using low viscosity alginic acid produced according to Preparations 1.

The invention is further defined by reference to the following examples, which are intended to be illustrative and not limiting.

The solubility rate and the paraquat-$Cl_2$ analysis were determined as follows. A hydrosulfite solution is prepared from 5.00 g sodium hydrosulfite, 2.00 g sodium hydroxide, and 93.00 g DI water. 1.00 g of dry product is dissolved in 999.0 g STW water and 1 ml samples are taken at 1, 2, 5, and 10 minutes. 1 ml sample is added to 98.0 g STW water and mixed. Then 1 ml hydrosulfite solution is added and mixed. Absorbance is read at 394 nm using a Pye Unicam Spectrophotometer SP1750. Absorbance of the test sample is matched with absorbance on control graph to give % Paraquat dichloride.

Synthetic Tap Water (STW) is deionized water containing 1000 ppm NaCl and 40 ppm $Ca^{++}$ (147 ppm $CaCl_2.2H_2O$).

EXAMPLE 1

Pan Agglomeration 30.0 g alginic acid (1600 cP, 10% solution) was placed in a pan agglomerator. 68.7 g of Paraquat CL (Chevron Chem. Co.), in a 29.1% active as the dichloride solution, was then sprayed (500 micron droplets) onto the moving acid bed, agglomerating the acid. After agglomeration, the mixture was treated with ammonia gas to a pH of 7.0–8.0, as measured on the damp granules. The complex granules were dried on a fluid bed dryer at an inlet temperature of 120° C. for 10 minutes, producing a free flowing granular product. This dry product showed no visible crystals or white fuzz on the surface of the granule. The solubility rate in STW water was 13 minutes.

EXAMPLE 2

Pan Agglomeration

Following the procedure of Example 1 but using 103.1 g of Paraquat CL in a 29.1% solution, a dry product was prepared.

This dry product showed no visible crystals or white fuzz on the surface of the granule. The solubility rate in STW water was 13 minutes.

EXAMPLE 3

Pan Agglomeration

Following the procedure of Example 1 but using 27.0 g of alginic acid (1600 cP, 10% solution), 8.7 g Paraquat CL in a 29.1% solution, and 3.0 g ethylenedinitrilotetraacetic acid (sequestrant), a dry product was prepared.

This dry product showed no visible crystals or white fuzz on the surface of the granule. The solubility rate in STW water was 10 minutes.

EXAMPLE 4

Drum Drying 15.0 g alginic acid (8cP, 10% solution) was blended with 30.0 g paraquat solution (43.5% active) and ammonium hydroxide as added to raise the pH to 7.0. A viscous paste was formed which was then drum dried using steam at 100° C. for the heat source. The algin/paraquat complex was then milled and screened to through 18 mesh on 40 mesh.

This dry product showed no visible crystals or white fuzz on the surface of particles. The solubility rate in STW water was less than 1 minute.

The amount of bipyridinium salt in the product was 43.2%, calculated as paraquat dichloride.

EXAMPLE 5

Drum Drying

Following the procedure of Example 4 but using 100.0 g of alginic acid (12 cP, 10% solution) and 300.0 g paraquat solution (43.5% active as dichloride) a dry product was prepared.

This dry product showed no visible crystals or white fuzz on the surface of particles. The solubility rate in STW water was less than 1 minute.

The amount of bipyridinium salt in the product was 45.0%, calculated as paraquat dichloride.

EXAMPLE 6

Pan Agglomeration

Following the procedure of Example 1 but using 15.0 g alginic acid (10 cP, 10% solution), blended with 15.0 g perlite (Dicaperl HP-200, Grefco, Inc.) and 55.0 g paraquat solution (43.5% active as dichloride) a dry product was prepared.

No crystals or white fuzz were visible on the surface of the particles. The rate of solubility was 1 minute. The perlite produced a floc.

EXAMPLE 7

Extremely Low Viscosity Ammonium Alginate 200 lbs. of low ash alginic acid (20% solids) was heated to 190° F. and held at temperature for 3 hours. 10 lbs. from above was neutralized with 28% ammonium hydroxide to a pH of 8.8. This product was then reheated to 180° F. with agitation for 8 hours which concentrated the liquid product. It was then tray dried for 72 hours at 180° F. and milled through 325 mesh. The final pH on the ammonium alginate product was 4.7 with a 10% viscosity of 12 cPs.

EXAMPLE 8

50% b.o.w. Paraquat Cation System Using Example 7 Ammonium Alginate:

| Formulation: | | |
|---|---|---|
| 30.00 g | 43.5% | paraquat dichloride solution |
| 1.00 g | 28% | ammonium hydroxide |
| 3.44 g | | ammonium alginate (12 cP at 10%) |

Procedure:

The ammonium hydroxide was first mixed with the paraquat solution. The ammonium alginate was then slowly added under agitation. This mixture was then heated with agitation to 180° F. for one hour to concentrate the system. This concentrate was then drum dried, milled and sized. The algin/paraquat complex was then tested for solubility and presence of paraquat crystals. The data is tabulated below:

| Data: | Appearance | Solubility | Paraquat Concentration |
|---|---|---|---|
| | no surface crystals | <1 minute | 48.5% cation |

EXAMPLE 9

50% b.o.w. Paraquat Cation System Using Extremely Low Viscosity Alginic Acid:

Formulation:

| | |
|---|---|
| 30.00 g | 43.5% paraquat dichloride solution |
| 2.50 g | 28% ammonium hydroxide |
| 3.34 g | alginic acid (15 cP at 10%) |

Procedure:

The ammonium hydroxide was first mixed with the paraquat solution. The alginate acid was then slowly added under agitation. This mixture was heated with agitation to 180° F. for one hour to concentrate the system. This concentrate was then drum dried, milled and sized. The algin/paraquat complex was then tested for solubility and presence of paraquat crystals.

| Data: | Appearance | Solubility | Paraquat Concentration |
|---|---|---|---|
| | no surface crystals | <1 minute | 48% cation |

For pan agglomeration techniques, it is possible to eliminate concentrating the algin/paraquat complex by increasing the viscosity of the alginate so that a 10% solution has a viscosity of 100–300 cP, preferably 150–250 cP. By using a higher viscosity alginate the solution of the complex is sufficiently viscous that it does not run off the hot drum when applied thereto. When dried on the drum, the complex is still rapidly soluble and crystal growth is prevented.

EXAMPLE 10

An alginic acid was treated as in Preparation 1 to produce a product with a viscosity of 200 cP at 10% concentration. The alginic acid was then used to produce a paraquat complex by drum drying.

Formulation:

| | |
|---|---|
| 30.00 g | 47.5% paraquat dichloride solution |
| 2.50 g | 28% ammonium hydroxide |
| 1.43 g | alginic acid (200 cP at 10%) |

Procedure:

The ammonium hydroxide was first mixed with the paraquat solution. The alginic acid was then slowly added under agitation. The mixture was agitated for one half hour to insure solubility of the alginic acid, and was then drum dried, milled and sized. The algin/paraquat complex was then tested for solubility and presence of paraquat crystals.

| Data: | Appearance | Solubility | Paraquat Concentration |
|---|---|---|---|
| | no surface crystals | <1 minute | 51% cation |

Thus, another embodiment of the invention is a high viscosity algin (alginic acid or salt or derivative thereof). By high viscosity is meant a 10% aqueous solution viscosity of 100 cP or higher; preferably 100–300 cP; more preferably 150–250 cP.

Claims to the invention follow.

What is claimed is:

1. A solid, herbicidal bipyridinium quaternary salt/algin complex comprising 14–52% (wt.) bipyridinium salt, calculated as cation, wherein the algin has a 10% solution viscosity of less than 20 cP and is alginic acid, sodium alginate, potassium alginate, ammonium alginate or propylene glycol alginate.

2. A complex of claim 1 wherein the bipyridinium salt is 1,1'-ethylene-2,2'-bipyridylium dibromide,
1,1'-dimethyl-4,4'-bipyridylium dichloride,
1,1'-di-2-hydroxyethyl-4,4'-bipyridylium dichloride,
1,1'-bis-3,5-dimethylmorpholinocarbonylmethyl-4,4'-bipyridylium dichloride
1-(2-hydroxyethyl)-1'-methyl-4,4'-bipyridylium dichloride,
1,1'-di-carbamoylmethyl-4,4'-bipyridylium dichloride,
1,1'-bis-N,N-dimethylcarbamoylmethyl-4,4'-bipyridylium dichloride,
1,1'-bis-N,N-diethylcarbamoylmethyl-4,4'-bipyridylium dichloride,
1,1-di-(piperidinocarbonylmethyl)-4,4'-bipyridylium dichloride,
1,1'-diacetonyl-4,4'-bipyridylium dichloride,
1,1'-diethoxycarbonylmethyl-4,4'-bipyridylium dibromide, or
1,1'-diallyl-4'-bipyridylium dibromide.

3. A complex of claim 1 wherein the algin has a 10% solution viscosity of about 15 cP or less.

4. A complex of claim 3 wherein the algin is alginic acid having a 10% solution viscosity of less than about 10 cP.

5. A complex of claim 3 wherein the algin is ammonium alginate.

6. A complex of claim 1 further comprising perlite, wherein the ratio of perlite to algin ranges from 3:1 to 1:3.

7. A process for preparing solid complexes of herbicidal bipyridinium salts and algin wherein the algin has a 10% solution viscosity of less than 20 cP and is alginic acid, sodium alginate, potassium alginate, ammonium alginate or propylene glycol alginate, which comprises:
   a. aqueously mixing and neutralizing algin and a bipyridinium salt to form a complex, and
   b. drying said complex.

8. A process of claim 7 wherein the algin in step (a) is first mixed with perlite in the ratio 3:1 to 1:3.

9. A process of claim 7 wherein the product of step (a) is drum dried, oven dried, or spray dried.

10. A process of claim 7 which comprises pan agglomerating algin and bipyridinium salt to form a mixture and neutralizing said mixture with ammonia.

* * * * *